United States Patent
O'Keefe et al.

(10) Patent No.: US 7,276,609 B2
(45) Date of Patent: Oct. 2, 2007

(54) PROCESS FOR PREPARING 4-(HYDROXY)-[1,4']BIPIPERIDINYL-L'CARBOXYLIC ACID TERT-BUTYL ESTER

(75) Inventors: Philip O'Keefe, Loughborough (GB); Mark Purdie, Loughborough (GB)

(73) Assignee: AstraZeneca AB, Södertalje (SE)

( * ) Notice: Subject to any disclaimer, the term of this patent is extended or adjusted under 35 U.S.C. 154(b) by 398 days.

(21) Appl. No.: 10/491,051

(22) PCT Filed: Oct. 2, 2002

(86) PCT No.: PCT/SE02/01802

§ 371 (c)(1),
(2), (4) Date: Mar. 29, 2004

(87) PCT Pub. No.: WO03/031433

PCT Pub. Date: Apr. 17, 2003

(65) Prior Publication Data

US 2004/0235895 A1    Nov. 25, 2004

(30) Foreign Application Priority Data

Oct. 5, 2001   (GB)   ................................. 0124020.9

(51) Int. Cl.
C07D 41/04   (2006.01)
(52) U.S. Cl. ...................................... 546/188; 546/187

(58) Field of Classification Search ................ 546/187, 546/188

See application file for complete search history.

(56) References Cited

U.S. PATENT DOCUMENTS

| 6,294,554 B1 | 9/2001 | Clader et al. ................ 514/316 |
| 6,387,899 B1 * | 5/2002 | Berg et al. ................. 514/235.8 |
| 6,525,070 B2 * | 2/2003 | Rigby et al. ................. 514/316 |

FOREIGN PATENT DOCUMENTS

| EP | 1070712 A1 | 1/2001 |
| WO | WO 01/77101 A1 | 10/2001 |

OTHER PUBLICATIONS

Assignment record US. 6,525,070.*
Assigment recort PCT/SE02/01802.*
Tsang et al. "Solid supported organotin hydrides for hydrogenation" CA 2000:794929 (2000).*
Zaluski et. al. "Hydrogenation properties of complex alkali metal hydrides . . . " J. Alloys and Compounds 290 p. 71-78 (1999).*

* cited by examiner

*Primary Examiner*—Celia Chang
(74) *Attorney, Agent, or Firm*—Fish & Richardson P.C.

(57) ABSTRACT

The present invention concerns a process for preparing 4-(hydroxy)-[1,4']bipiperidinyl-1'-carboxylic acid tert-butyl ester, comprising hydrogenating a mixture of 4-hydroxypiperidine and 1-tert-butoxycarbonyl-4-piperidone in a suitable solvent, in the presence of a suitable catalyst and at a suitable pressure.

10 Claims, No Drawings

PROCESS FOR PREPARING 4-(HYDROXY)-[1,4']BIPIPERIDINYL-L'CARBOXYLIC ACID TERT-BUTYL ESTER

This application claims priority under 35 U.S.C. § 371 to a national phase filing of international application number PCT/SE02/01802, filed Oct. 2, 2002, which claims priority to GB 0124020.9, filed Oct. 5, 2001. These applications are incorporated by reference herein.

The present invention concerns a process for preparing 4-(hydroxy)-[1,4']bipiperidinyl-1'-carboxylic acid tert-butyl ester.

[1,4']Bipiperidinyl-1'-yl derivatives are disclosed in WO 01/77101 (PCT/SE01/00751) as modulators of CCR3 chemokine receptor activity. 4-(Hydroxy)-[1,4']bipiperidinyl-1'-carboxylic acid tert-butyl ester can be used in the preparation of some such compounds.

The present invention provides a process for the preparation of 4-(hydroxy)-[1,4']bipiperidinyl-1'-carboxylic acid tert-butyl ester that has the formula (I):

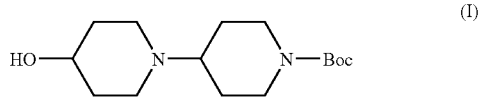

wherein Boc is tert-butoxycarbonyl, comprising hydrogenating a mixture of 4-hydroxypiperidine and a compound of formula (II):

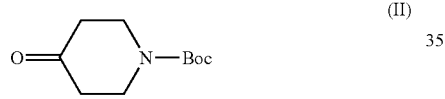

in a suitable solvent, in the presence of a suitable catalyst and at a suitable pressure.

The compound of formula (I) can be named as 4-(hydroxy)-[1,4']bipiperidinyl-1'-carboxylic acid tert-butyl ester, while the compound of formula (II) can be named as 1-tert-butoxycarbonyl-4-piperidone.

The source of hydrogen for the hydrogenation can be from an external source (such as a cylinder of hydrogen) or, alternatively, hydrogen can be produced in situ (a transfer hydrogenation; for example by the degradation of formic acid to hydrogen and carbon dioxide).

Suitable solvents are, for example, an aliphatic alcohol (such as a $C_{1-6}$ carbon aliphatic alcohol, for example ethanol) or an ether (such as tetrahydrofuran), or a mixture of such solvents (for example a mixture of ethanol and tetrahydrofuran). The carbon chains of the aliphatic alcohols are straight or branched. The solvent is preferably a $C_{1-6}$ carbon aliphatic alcohol, especially ethanol.

Suitable catalysts are, for example, a palladium or platinum catalyst, especially palladium or platinum supported on carbon. Suitable catalysts preferably comprise 2-15% (especially 4-12%) metal and include 5% palladium on carbon (such as Johnson Matthey types 437, 440, 331, 38H, 39, 398, 472, 58 and 87L; or Engelhard type 5214), 10% palladium on carbon (such as Johnson Matthey type 87L), 5% platinum on carbon (such as Johnson Matthey type 117) or a mixture of palladium and platinum on carbon for example 2.5% palladium, 2.5% platinum on carbon (such as Johnson-Matthey catalyst 5R/121). A catalyst loading of between 10 wt % and 40 wt % of catalyst (with respect to 4-hydroxypipenidine) is preferred.

A suitable pressure is, for example, a pressure of between 1 and 5 bar (especially between 2 and 5 bar).

The process of the present invention can be conducted in the presence of a suitable acid (such as a $C_{1-6}$ carbon acid (such as formic acid or acetic acid), wherein the carbon chains of the acid is straight or branched). A preferred acid is acetic acid.

It is preferred that the process is conducted at ambient temperature (such as 10-30° C.).

A compound of formula (III):

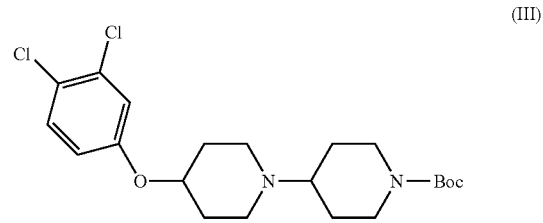

can be prepared by reacting a compound of formula (I):

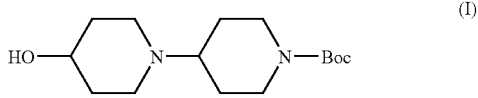

with 3,4-dichlorofluorobenzene in the presence of a suitable a suitable base (such as an alkali metal (especially potassium) tert-butoxide) in a suitable solvent (such as an ether, for example tetrahydrofuran) at an elevated temperature (such as in the range 50-100° C., for example at about 70° C. or at the boiling point of the solvent used).

Thus, in a fitter aspect the present invention provides a process for preparing a compound of formula (III) comprising:

1. reacting 4-hydroxypiperidine with a compound of formula (II) by the process described above to obtain a compound of formula (I); and,
2. reacting the compound of formula (I) with 3,4-dichlorofluorobenzene using the process described above.

The invention will now be illustrated by the following non-limiting Examples. In the Examples the following apply, unless stated otherwise:

(i) when given, $^1$H NMR data is quoted and is in the form of delta values for major diagnostic protons, given in parts per million (ppm) relative to tetramethylsilane (TMS) as an internal standard, determined at 300 MHz or 400 MHz using perdeuterio DMSO-D6 ($CD_3SOCD_3$) or $CDCl_3$ as the solvent unless otherwise stated;

(ii) mass spectra (MS) were run with an electron energy of 70 electron volts in the chemical ionisation (CI) mode using a direct exposure probe; where values for m/z are given, generally only ions which indicate the parent mass are reported, and unless otherwise stated the mass ion quoted is the positive mass ion—$(M+H)^+$; and, (iii) the following abbreviations are used:

| | |
|---|---|
| Boc or BOC | tert-butoxycarbonyl |
| MTBE | tert-butyl methyl ether |
| THF | tetrahydrofuran |
| HPLC | high performance liquid chromatography |

EXAMPLE 1

This Example illustrates the preparation of 4-(3,4-dichlorophenoxy)-[1,4']bipiperidinyl-1'-carboxylic acid tert-butyl ester.

1-tert-Butoxycarbonyl-4-piperidone (55 g, 0.276 mol, 1.15 eq) and 4-hydroxypiperidine (24.3 g, 0.24 mol, 1 eq) were stirred at room temperature in ethanol (160 ml) and acetic acid (16 ml) for 25 minutes. To the solution was added 2.4 g of 5% palladium on carbon type 87L Johnson Matthey catalyst. The reaction was then hydrogenated under a pressure of 3.5 bar at room temperature for 72 hours. The catalyst was filtered off and the mixture partitioned between water (320 ml) and iso-propyl acetate (360 ml). The aqueous was collected, and washed twice further with iso-propyl acetate (2×360 ml). The aqueous was then basified (10M aqueous sodium hydroxide, 25 ml) and the aqueous washed twice with MTBE (2×194 ml). Solvent (194 ml) was removed by distillation under vacuum (−0.7 bar, 65° C. oil bath). THF (777 ml) was added and the solution again concentrated by removal of solvent (777 ml, −0.7 bar, 65° C. oil bath). THF (485 ml) was added to the solution and solvent (485 ml) removed by vacuum distillation (−0.7 bar, 70° C.). Half of the solution was evaporated at this point to give 4-(hydroxy)-[1,4']bipiperidinyl-1'-carboxylic acid tert-butyl ester as an off-white solid (25.31 g, 74% yield; 99.6% purity HPLC area %).

$^1$H NMR (300 MHz, CDCl$_3$) δ 1.34-1.48 (11H, m), 1.52-1.66 (3H, m), 1.75-1.93 (4H, m), 2.26-2.45 (3H, m), 2.64-2.85 (4H, m), 3.64-3.72 (1H,m), 4.10-4.25 (2H, d). MS: m/z (M+H)$^+$ 285.

The other half of the solution (containing approximately 25.3 g of 4-(hydroxy)-[1,4']bipiperidinyl-1'-carboxylic acid tert-butyl ester) was diluted with THF (80 ml). A suspension of potassium tert-butoxide (2 eq, 26.9 g) in THF (88 ml) was added, and the reaction stirred at room temperature for 20 minutes. 3,4-Dichlorofluorobenzene (1.2 eq, 17 ml (total volume)) was added followed by THF (80 ml). The reaction mixture was warmed to 50° C. and maintained at this temperature for 10 minutes. The reaction mixture was then heated to reflux (temperature 68° C.) for 150 minutes after which it was cooled to room temperature, and water (136 ml) added. The layers were separated and the organic collected. Solvent (221 ml) was removed from the organic layer by distillation (−0.7 bar, 32° C. distillate) and the remainder was cooled to room temperature. Heptane (374 ml) was added and the layers separated. The organic was collected. Solvent (374 ml) was removed by distillation (−0.8 bar, 40° C. distillate). Heptane (187 ml) was added, then solvent (136 ml) removed by vacuum distillation (−0.8 bar, 44° C. distillate). The reaction mixture was cooled to room temperature and stirred at this temperature for 18 hours, and then at 0-5° C. for 3 hours. A solid separated. The solid was filtered and washed with cold heptane (50 ml). The solid was dried under vacuum at 40° C. for 18 hours, yielding the tide compound as a white solid (28.6 g, 55.5% yield (over 2 steps), 94.6% purity by HPLC).

$^1$H NMR (300 Mz CDCl$_3$) δ 1.33-1.49 (11H, m), 1.76-1.84 (4H, m), 1.95-2.0 (2H, m), 2.40-2.47 (3H, m), 2.69-2.83 (4H, m), 4.13-4.28 (3H,m), 6.73-6.77 (1H,d), 6.99-7.00 (1H,s), 7.29-7.32 (1H,d). MS: m/z (M+H)$^+$ 430.

EXAMPLE 2

This Example illustrates the preparation of 4-(hydroxy)-[1,4']bipiperidinyl-1'-carboxylic acid tert-butyl ester.

4-Hydroxypiperidine (0.254 g, 2.51 mmol) and N-Boc-piperidone (0.5 g, 2.51 mmol, 1 eq) were dissolved in ethanol (5 ml) and stirred at room temperature for 5 minutes. To this stirred solution was added 10% palladium on carbon (0.5 g) and formic acid (0.5 ml, 5 eq) and the reaction stirred at room temperature for 102 hours. The reaction was stopped and filtered through CELITE™. The catalyst was washed with ethanol (50 ml) and the filtrates evaporated to give the title compound as a yellow oil (0.69 g, 97% yield; 76% purity by HPLC area).

EXAMPLE 3

This Example illustrates the preparation of 4-(3,4-dichlorophenoxy)-[1,4']bipiperidinyl-1'-carboxylic acid tert-butyl ester, using 5% Pd on C (Type 437) catalyst.

1-tert-Butoxycarbonyl-4-piperidone (4.02 g, 0.0217 mol, 1.3 eq) and 4-hydroxypiperidine (1.57 g, 0.0155 mol, 1 eq) were stirred at room temperature in ethanol (18 ml) and acetic acid (2 ml) for 10 minutes. To the solution was added 0.62 g of 5% palladium on carbon type 437 Johnson Matthey catalyst. The reaction was then hydrogenated under a pressure of between 4 and 4.5 bar at room temperature for 26 hours. The catalyst was filtered off through CELITE™, washed with ethanol (40 ml) and evaporated in vacuo to an oil. To the oil was added acetic acid (1 ml) and the oil partitioned between water (20 ml) and dichloromethane (30 ml). The aqueous was collected and basified (5M aqueous sodium hydroxide, 5 ml) and the aqueous washed twice with dichloromethane (2×20 ml). The combined organics were washed with brine and dried (magnesium sulphate). The solution was filtered and evaporated in vacuo to give 4-(hydroxy)-[1,4']bipiperidinyl-1'-carboxylic acid tert-butyl ester as a yellow oil (2.03 g, 46% yield; 92.1% purity HPLC area %).

EXAMPLE 4

This Example illustrates the preparation of 4-(3,4-dichlorophenoxy)-[1,4']bipiperidinyl-1'-carboxylic acid tert-butyl ester, using 5% Pd on C (Type 38H) catalyst.

1-tert-Butoxycarbonyl-4-piperidone (3.94 g, 0.0198 mol, 1 eq) and 4-hydroxypiperidine (2 g, 0.0198 mol, 1 eq) were stirred at room temperature in ethanol (20 ml) and acetic acid (4 ml) for 3 hours. To the solution was added 0.6 g of 5% palladium on carbon type 38H Johnson Matthey catalyst The reaction was then hydrogenated under a pressure of 4 bar at room temperature for 68 hours. The catalyst was filtered off through CELITE™, washed with ethanol (60 ml) and evaporated in vacuo to an oil. To the oil was added 10% citric acid (7 ml), water (10 ml) and dichloromethane (40 ml). The aqueous was collected and basified (5M aqueous sodium hydroxide, 12 ml) and the aqueous washed twice with dichloromethane (2×30 ml). The combined organics were washed with brine and dried (magnesium sulphate). The solution was filtered and evaporated in vacuo to give 4-(hydroxy)-[1,4']bipiperidinyl-1'-carboxylic acid tert-butyl ester as a yellow oil (4.35 g, 77% yield; 90% purity HPLC area %).

EXAMPLE 5

This Example illustrates the preparation of 4-(3,4dichlorophenoxy)-[1,4']bipiperidinyl-1'-carboxylic acid tert-butyl ester, using 5% Pd on C (Type 440) catalyst.

1-tert-Butoxycarbonyl-4-piperidone (4 g, 0.0201 mol, 1.3 eq) and 4-hydroxypiperidine (1.56 g, 0.054 mol, 1 eq) were stirred at room temperature in ethanol (20 ml) and acetic acid (2 ml) for 3 hours. To the solution was added 0.56 g of 5% palladium on carbon type 440 Johnson Matthey catalyst. The reaction was then hydrogenated under a pressure of 3 bar at room temperature for 16 hours. The catalyst was filtered off through CELITE™, washed with ethanol (40 ml) and evaporated in vacuo to an oil. The oil was dissolved in water (25 ml) and the aqueous washed twice with dichloromethane (2×20 ml). The aqueous was basified (5M aqueous sodium hydroxide, 12 ml) and the aqueous washed twice with dichloromethane (2×30 ml). The combined organics were dried (magnesium sulphate). The solution was filtered and evaporated in vacuo to give 4-(hydroxy)-[1,4']bipiperidinyl-1'-carboxylic acid tert-butyl ester as a yellow oil (3.13 g, 71.5% yield, 95.4% purity HPLC area %).

EXAMPLE 6

This Example illustrates the preparation of 4-(3,4-dichlorophenoxy)-[1,4']bipiperidinyl-1'-carboxylic acid tert-butyl ester, using 5% Pd on C Engelhard catalyst (Type 5214) catalyst.

1-tert-Butoxycarbonyl-4-piperidone (6.87 g, 0.0345 mol, 1.15 eq) and 4-hydroxypiperidine (3.03 g, 0.03 mol, 1 eq) were stirred at room temperature in ethanol (25 ml) and acetic acid (2 ml) for 2 hours. To the solution was added 0.3 g of 5% palladium on carbon type 5214 Engelhard catalyst. The reaction was then hydrogenated under a pressure of 3.5 bar at room temperature for 24 hours. Further catalyst (0.3 g) was added and the reaction hydrogenated under a pressure of 3.5 bar for a further 19 hours. The catalyst was filtered off through CELITE™, washed with ethanol (10 ml) and evaporated in vacuo to an oil. To the oil was added 20% citric acid (10 ml) and isopropyl acetate (20 ml). The aqueous was collected and basified (10M aqueous sodium hydroxide, 3 ml) and the aqueous washed twice with MTBE (2×25 ml). The combined organics were washed with brine and dried (magnesium sulphate). The solution was filtered and evaporated in vacuo to give 4-(hydroxy)-[1,4']bipiperidinyl-1'-carboxylic acid tert-butyl ester as a yellow oil (6.9 g, 79.8% yield; 96.3% purity HPLC area %).

EXAMPLE 7

This Example illustrates the preparation of 4-(3,4-dichlorophenoxy)-[1,4']bipiperidinyl-1'-carboxylic acid tert-butyl ester, using 5% Pt on C (Type 117) catalyst.

1-tert-Butoxycarbonyl-4-piperidone (3 g, 0.0151 mol, 1 eq) and 4-hydroxypiperidine (1.56 g, 0.0154 mol, 1 eq) were stirred at room temperature in ethanol (10 ml) and acetic acid (1 ml) for 30 minutes. To the solution was added 0.4 g of 5% platinum on carbon type 117 Johnson Matthey catalyst. The reaction was then hydrogenated under a pressure of 3 bar at room temperature for 6 hours. The reaction was filtered through CELITE™ and washed with ethanol (40 ml). The 4-(hydroxy)-[1,4']bipiperidinyl-1'-carboxylic acid tert-butyl ester (13.7% purity by HPLC area %) was not isolated.

EXAMPLE 8

This Example illustrates the preparation of 4-(3,4-dichlorophenoxy)-[1,4']bipiperidinyl-1'-carboxylic acid tert-butyl ester, using 5% Pd on C (Type 87L) catalyst.

1-tert-Butoxycarbonyl-4-piperidone (3.43 g, 0.0171 mol, 1.15 eq) and 4-hydroxypiperidine (1.51 g, 0.0149 mol, 1 eq) were stirred at room temperature in THF (20 ml), ethanol (3 ml) and acetic acid (0.4 ml) for 4 hours. To the solution was added 0.4 g of 5% palladium on carbon type 87L Johnson Matthey catalyst The reaction was then hydrogenated under a pressure of 2.5 bar at room temperature for 19 hours. The catalyst was filtered off through CELITE™ and washed with ethanol (20 ml). The 4-(hydroxy)-[1,4']bipiperidinyl-1'-carboxylic acid tert-butyl ester (50% purity by HPLC area %) was not isolated.

EXAMPLE 9

This Example illustrates the preparation of 4-(3,4-dichlorophenoxy)-[1,4']bipiperidinyl-1'-carboxylic acid tert-butyl ester, using 5% Pd on C (Type 87L) catalyst.

1-tert-Butoxycarbonyl-4-piperidone (2.29 g, 0.0114 mol, 1.15 eq) and 4-hydroxypiperidine (1 g, 0.0099 mol, 1 eq) were stirred at room temperature in THF (10 ml) and acetic acid (0.6 ml) for 20 hours. To the solution was added 0.17 g of 5% palladium on carbon type 87L Johnson Matthey catalyst. The reaction was then hydrogenated under a pressure of 3 bar at room temperature for 24 hours. The catalyst was filtered off through CELITE™ and washed with THF (20 ml). The 4-(hydroxy)-[1,4']bipiperidinyl-1'-carboxylic acid tert-butyl ester (18.8% purity by HPLC area %) was not isolated.

EXAMPLE 10

The examples in table 1 illustrate the preparation of 4-(3,4-dichlorophenoxy)-[1,4']bipiperidinyl-1'-carboxylic acid tert-butyl ester, using various 5% and 10% Pd on C catalysts.

General Method 1-tert-Butoxycarbonyl-4-piperidone (0.5 g, 0.0025 mol, 1 eq) and 4-hydroxypiperidine (0.254 g, 0.0025 mol, 1 eq) were stirred at room temperature in ethanol (5 ml) and acetic acid (0-0.5 ml—see Table 1) for 2 hours. To the solution was added 0.1 g of a 5 or 10% palladium on carbon type Johnson Matthey catalyst. The reaction mixture was then hydrogenated under a pressure of 3-4 bar at room temperature for 23 hours and then analysed by HPLC.

The results are shown in Table 1. 4-(Hydroxy)-[1,4']bipiperidinyl-1'-carboxylic acid tert-butyl ester (Product in Table 1) was not isolated.

TABLE 1

| | | Results by HPLC area % | |
| --- | --- | --- | --- |
| Catalyst | Acetic acid | Product | Starting material N-Boc-4-piperidone |
| 5% Pd on C Type 58 | 0.5 ml | 56.5 | 14.0 |
| 5% Pd on C Type 38H | 0.5 ml | 51.7 | 43.6 |
| 5% Pd on C Type 472 | 0.5 ml | 47.1 | 38.2 |
| 5% Pd on C Type 331 | 0.5 ml | 52.1 | 41.5 |
| 5% Pd on C Type 440 | 0.5 ml | 55.8 | 8.0 |
| 5% Pd on C Type 440 | 0 ml | 53.7 | 0 |
| 5% Pd on C Type 87L | 0.5 ml | 63.7 | 17.4 |
| 5% Pd on C Type 39 | 0.5 ml | 63.4 | 17.4 |
| 10% Pd on C Type 87L | 0.5 ml | 58.8 | 19.4 |
| 10% Pd on C Type 87L | 0 ml | 48.2 | 5.3 |

The invention claimed is:

1. A process for the preparation of a compound of formula (I):

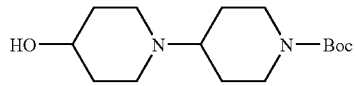
(I)

wherein Boc is tert-butoxycarbonyl, comprising catalytic hydrogenation, by $H_2$, of a mixture of 4-hydroxypiperidine and a compound of formula (II):

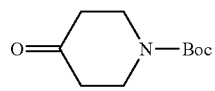
(II)

in a suitable solvent, in the presence of palladium and/or platinum catalyst and at a suitable pressure.

2. A process as claimed in claim 1 wherein the solvent is an aliphatic alcohol, an ether or a mixture of two such solvents.

3. A process as claimed in claim 1 wherein the catalyst is a palladium catalyst.

4. A process as claimed in claim 3 wherein the catalyst is 5% palladium on carbon or 10% palladium on carbon.

5. A process as claimed in claim 1 wherein a catalyst loading of between 10 wt % and 40 wt % of catalyst, with respect to 4-hydroxypiperidine, is used in the process.

6. A process as claimed in claim 1 wherein a suitable acid is also present for the process.

7. A process as claimed in claim 6 wherein the acid is acetic acid.

8. A process as claimed in claim 1 wherein the pressure is between 1 and 5 bar.

9. A process as claimed in claim 1 wherein the process is conducted at 10-30° C.

10. A process for preparing a compound of formula (III):

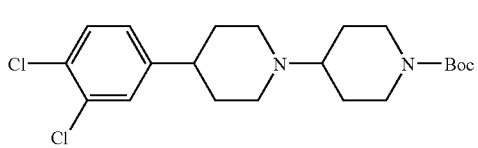
(III)

comprising the steps of:

a. catalytic hydrogenation, by $H_2$, of a mixture of 4-hydroxypiperidine and a compound of formula (II):

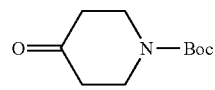
(II)

in a suitable solvent, in the presence of palladium and/or platinum catalyst and at a suitable pressure to form a compound of formula (I):

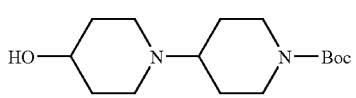
(I)

and, b. reacting the compound of the formula (I) with 3,4-dichlorofluorobenzene in the presence of a suitable base in a suitable solvent at an elevated temperature.

* * * * *

UNITED STATES PATENT AND TRADEMARK OFFICE
CERTIFICATE OF CORRECTION

PATENT NO.        : 7,276,609 B2
APPLICATION NO. : 10/491051
DATED             : October 2, 2007
INVENTOR(S)       : Philip O'Keefe It is certified that error appears in the above-identified patent and that said Letters Patent is hereby corrected as shown below:

<u>On the Title Page Item -54- Title:</u>

Should read: "A PROCESS FOR PREPARING 4-(HYDROXY)-[1,4'] BIPIPERIDINYL-1'CARBOXYLIC ACID TERT-BUTYL ESTER"

<u>Col. 7 Claim 3, Line 28 should read</u>:

between "palladium" and "catalyst", insert -- or platinum --

Signed and Sealed this

Sixth Day of January, 2009

JON W. DUDAS
*Director of the United States Patent and Trademark Office*

UNITED STATES PATENT AND TRADEMARK OFFICE
CERTIFICATE OF CORRECTION

PATENT NO. : 7,276,609 B2
APPLICATION NO. : 10/491051
DATED : October 2, 2007
INVENTOR(S) : Philip O'Keefe It is certified that error appears in the above-identified patent and that said Letters Patent is hereby corrected as shown below:

<u>On the Title Page Item -54- and Column 1, lines 1-3, Title:</u>

Should read: "A PROCESS FOR PREPARING 4-(HYDROXY)-[1,4'] BIPIPERIDINYL-1'CARBOXYLIC ACID TERT-BUTYL ESTER"

<u>Col. 7 Claim 3, Line 28 should read:</u> between "palladium" and "catalyst", insert -- or platinum --

This certificate supersedes the Certificate of Correction issued January 6, 2009.

Signed and Sealed this

Third Day of February, 2009

JOHN DOLL
*Acting Director of the United States Patent and Trademark Office*